(12) United States Patent
Kettwig et al.

(10) Patent No.: US 9,180,027 B2
(45) Date of Patent: Nov. 10, 2015

(54) ORTHOPEDIC INTERFACE

(75) Inventors: Thomas Kettwig, Goettingen (DE); Sven Zarling, Duderstadt (DE); Bernard Garus, Enibeck (DE); Felix Ruess, Goettingen (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 637 days.

(21) Appl. No.: 12/670,465

(22) PCT Filed: Jul. 10, 2008

(86) PCT No.: PCT/DE2008/001124
§ 371 (c)(1),
(2), (4) Date: Jul. 14, 2010

(87) PCT Pub. No.: WO2009/015627
PCT Pub. Date: Feb. 5, 2009

(65) Prior Publication Data
US 2010/0318195 A1 Dec. 16, 2010

(30) Foreign Application Priority Data
Jul. 26, 2007 (DE) .......................... 10 2007 035 409

(51) Int. Cl.
*A61F 2/78* (2006.01)
*A61B 5/0408* (2006.01)
*A61B 5/00* (2006.01)
(Continued)

(52) U.S. Cl.
CPC .............. *A61F 2/7812* (2013.01); *A61B 5/0408* (2013.01); *A61B 5/6804* (2013.01); *A61N 1/0452* (2013.01); *A61N 1/0456* (2013.01); *A61N 1/0472* (2013.01); *A61N 1/0484* (2013.01); *D04B 1/265* (2013.01); *A61F 2/0077* (2013.01); *A61F 2002/3007* (2013.01); *A61F 2002/30024* (2013.01); *A61F 2002/705* (2013.01); *A61F 2250/0021* (2013.01); *A61F 2310/0052* (2013.01)

(58) Field of Classification Search
CPC ........... A61F 2/7812; A61F 2002/7818; A61F 2002/30024; A61F 2250/0021; A61F 2002/7881; A61F 2002/7837
USPC .......................................................... 623/36
See application file for complete search history.

(56) References Cited

U.S. PATENT DOCUMENTS 5,007,937 A 4/1991 Fishman et al.
5,413,611 A 5/1995 Haslam et al.
(Continued)

FOREIGN PATENT DOCUMENTS

BY 8908 C1 8/2009
DE 40 33 633 10/1990
(Continued)

*Primary Examiner* — Bruce E Snow
*Assistant Examiner* — Melissa Hoban
(74) *Attorney, Agent, or Firm* — Whitham, Curtis, Christofferson & Cook PC; Michael E. Whitham

(57) ABSTRACT

The invention relates to an orthopedic interface (1) comprising a planar 3D textile (2) having a top (22) and a bottom (21), which are held at a distance from each other by supporting threads (24) and are connected to each other, wherein the bottom (21) of the spaced knitted fabric (2) is configured for resting on the skin of an interface user. The side of the bottom (21) facing the skin is provided with an adhesive coating (23) at least in some regions.

22 Claims, 3 Drawing Sheets

(51) Int. Cl.
*A61N 1/04* (2006.01)
*D04B 1/26* (2006.01)
*A61F 2/00* (2006.01)
*A61F 2/30* (2006.01)
*A61F 2/70* (2006.01)

(56) References Cited

U.S. PATENT DOCUMENTS

| | | | |
|---|---|---|---|
| 5,419,755 A * | 5/1995 | Fukumoto et al. | 602/23 |
| 5,443,525 A | 8/1995 | Laghi | |
| 5,807,295 A | 9/1998 | Hutcheon | |
| 6,139,513 A | 10/2000 | Grim et al. | |
| 6,499,320 B1 | 12/2002 | Bernhardt | |
| 2001/0007929 A1 | 7/2001 | Schlomski | |
| 2002/0183859 A1 | 12/2002 | Houser | |
| 2003/0194935 A1 | 10/2003 | Schlomski et al. | |
| 2006/0079964 A1 * | 4/2006 | Perkins et al. | 623/36 |
| 2006/0089725 A1 * | 4/2006 | Kurth | 623/36 |
| 2007/0225824 A1 * | 9/2007 | Einarsson | 623/36 |
| 2007/0264482 A1 * | 11/2007 | Banker et al. | 428/223 |
| 2010/0004756 A1 * | 1/2010 | Horie | 623/36 |

FOREIGN PATENT DOCUMENTS

| | | |
|---|---|---|
| DE | 195 31 070 | 8/1995 |
| DE | 202 05 706 | 4/2002 |
| DE | 102 19 814 | 5/2002 |
| JP | 3059107 | 3/1999 |
| JP | 2001-252297 A | 9/2001 |
| WO | WO 96/21405 | 7/1996 |
| WO | WO 99/65434 | 12/1999 |
| WO | EP 1 052 319 | 4/2000 |
| WO | EP 1 114 630 | 12/2000 |
| WO | WO 01-67984 | 9/2001 |
| WO | WO 2004-060136 | 7/2004 |
| WO | WO 2005/052235 | 6/2005 |
| WO | 2006/015599 A1 | 2/2006 |
| WO | 2006/120498 A2 | 11/2006 |

* cited by examiner

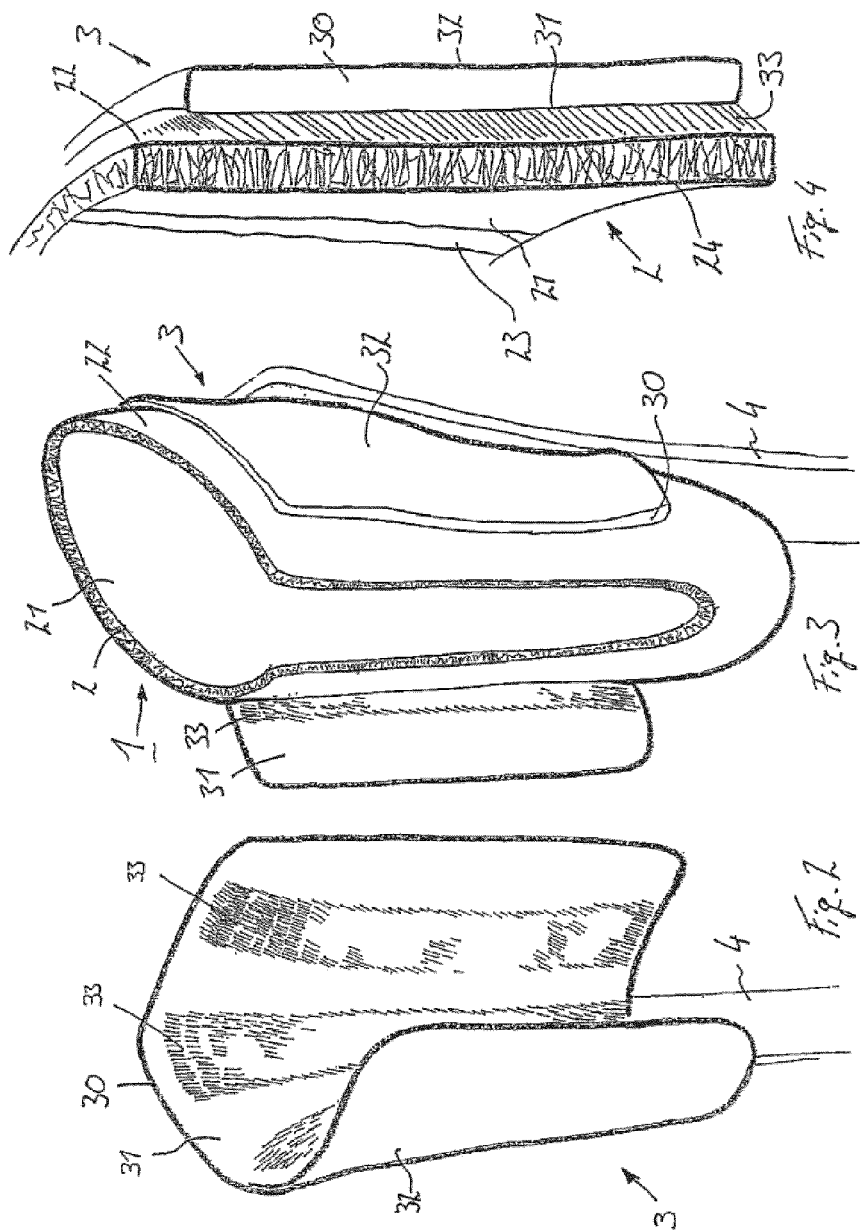

ORTHOPEDIC INTERFACE

The invention relates: to an orthopedic interface comprising a planar 3D textile with a top and a bottom that are held at a distance from each other by supporting threads and connected to each other, the bottom of the 3D textile being designed to bear on the skin of an interface user, and a system composed of an orthopedic interface and of an orthotic or prosthetic device.

DE 102: 13 814 B4 discloses a physiological sleeve which is designed to: be applied to a human limb and which, when being worn, is stretched and adapted to the body shape. At a defined pressure, the applied sleeve compresses the muscle tissue, said sleeve being made of a spaced knitted fabric with elastic threads. By applying the sleeve, an increased flow of blood, through the muscle tissue is achieved at a state of rest. The sleeve serves to improve the fitness of the wearer and not as an orthopedic interface.

The prior art also discloses liners made of silicone or of a copolymer, which are worn over an amputation stump in order to produce a cushioned and air-tight coupling between an amputation stump and a prosthesis socket. Liners are also known that are made of polyurethane and that are worn directly on the skin of the interface user.

The object of the present invention is to make available an orthopedic interface and a system composed of an interface and of an orthotic or prosthetic device, with which it is possible to provide greater ease of use and a higher level of comfort.

According to the invention, this object is achieved by an orthopedic interface having the features of claim 1 and by a system having the features of claim 19.

Advantageous embodiments and developments of the inventions are set forth in the dependent claims, The orthopedic interface according to the invention, comprising a planar 3D textile with a top and a bottom that are held at a distance from each other by supporting threads and connected to each other, the bottom of the 3D textile being designed to bear on the skin of an interface user, is characterized in that the surface or side of the bottom facing the skin is provided at least partially with an adhesive coating, that is to say a coating that adheres to the skin, in order to ensure the orientation of the orthopedic interface with respect to the body part, for example an amputation stump or a limb that is to foe supported by an orthosis. The 3D textile provides improved comfort by distributing punctiform pressure forces. Moreover, 3D textiles are able to breathe and permit a natural exchange of liquid via the skin.

The invention also proposes that the outer face of the orthopedic interface, that is to say the surface of the top, is provided at least partially with a coating that promotes increased adherence on the orthopedic interface. The coating or coatings can be composed, for example, of silicone, polyurethane or a copolymer, thus resulting in improved adhesion to the skin and also to other orthopedic components, such as orthoses or prostheses. The coating can also be electrically conductive, in order to stimulate the skin surface, to carry off potentials, or to forward signals, for example on the outer face of the 3D textile. The signals can be transmitted, for example, to sensors or evaluation devices.

The coating or coatings can be applied in areas set apart from each other on the respective surfaces of the top and/or bottom, for example in the shape of strips, dots, rings, or in other planar shapes. It is likewise possible for a corresponding coating to be applied to the surfaces only in particularly stressed areas of the orthopedic interface, whereas less stressed areas are not provided with a coating. This increases the level of comfort and improves the exchange of heat and of moisture from the skin through the interface to the environment. Alternatively, the coating or coatings are applied over the whole surface in order to ensure a maximum hold of the interface. The coating can be moisture-permeable in order to maintain an exchange of moisture. The coating materials are accordingly chosen for this purpose, for example in the form of, polyurethane or of a copolymer. Large areas of the coatings can likewise be provided with perforations in order to allow air and water to pass through. Even in the case of the whole surface being coated, it is possible to permit an exchange of gas and moisture, for example since thin silicone coatings have been found to be able to breathe. Additional thermal insulation is afforded by the layer of air located between the top and bottom in the 3D textile.

The processed threads of the 3D textile can also be coated separately, in order to meet special requirements of the textile. The coatings can provide improved skin compatibility or improved transport of moisture, in order thereby to further increase the comfort of the interface.

To improve the skin compatibility, the coating of the threads or of the interface can be soaked with an antibacterial agent, and it is likewise possible for silver threads to be woven or spun into the bottom or the 3D textile in order to improve the skin compatibility. It is also possible for silver to be vapor-deposited onto, or for silver ions to be added to, the 3D textile or the coating or coatings.

Instead of or in addition to an adhesive coating, the top, that is to say the outer surface of the orthopedic interface, can be provided with a structure that has less resistance in the direction of insertion of the interface than counter to the direction of insertion. The structure can be designed or applied as a nap velour by way of which a coupling to an orthopedic component, for example an outer socket or an orthosis holder, can be established. For this purpose, the textile or the structure or coating is inclined in one direction to make it easier to slide into the receiving device for the limb, while effectively preventing slipping out. To release the coupling between the interface and the orthopedic component, the holder is released, for example bent out or folded open.

The orthopedic interface can foe designed as a liner for bearing on an amputation stump, and it is likewise possible for it to be designed as a flexible socket or as a flexible socket part and have receiving means for orthotic or prosthetic components.

To make the orthopedic interface easier to apply, it is preferably anatomically preshaped, and it can likewise have an open cross section and be applied using closing devices, such as velcro closures or the like.

The 3D textile is preferably designed as a spaced knitted fabric. The top of the spaced knitted fabric preferably has an upper textile and the bottom, that is to say the surface directed toward the skin of the interface user, has a so-called lower textile. The upper and lower textiles form the ends of the spaced knitted fabric and the contact faces with respect to the orthosis or prosthesis and to the skin.

In a development of the invention, electrodes are applied to the inner surface of the interface or are worked into the 3D textile, in order to carry off muscle signals or nerve signals or to stimulate muscles or nerves. The electrodes can be applied in various ways, i.e. embroidered, sewn, adhesively bonded or welded.

The system, according to the invention is composed of an interface, of the kind described above, and of an orthotic or prosthetic device coupled, thereto, which device can be secured to the upper textile or outer surface of the interface by coupling means. The orthotic or prosthetic device can have a substantially dimensionally stable receiver with an inner coating, which coating can be composed of an adhesive material, for example silicone, polyurethane or copolymer or another coating, for example velcro closure elements or a nap velour, in order to achieve a coupling of the dimensionally stable receiver to the interface. Alternatively or in addition, the surface of the receiver directed toward the interface can have a structure that has low resistance to insertion and a high resistance counter to the direction of insertion. The structure can be composed of suitably oriented form-fit elements or the like.

Illustrative embodiments of the invention are explained in more detail below with reference to the attached figures, in which:

FIG. 2 shows a perspective partial view of a prosthetic device;

FIG. 3 shows a prosthetic device according to FIG. 2 with interface;

FIG. 4 shows an enlarged cross-sectional view through an interface and a receiver.

Figure 1:
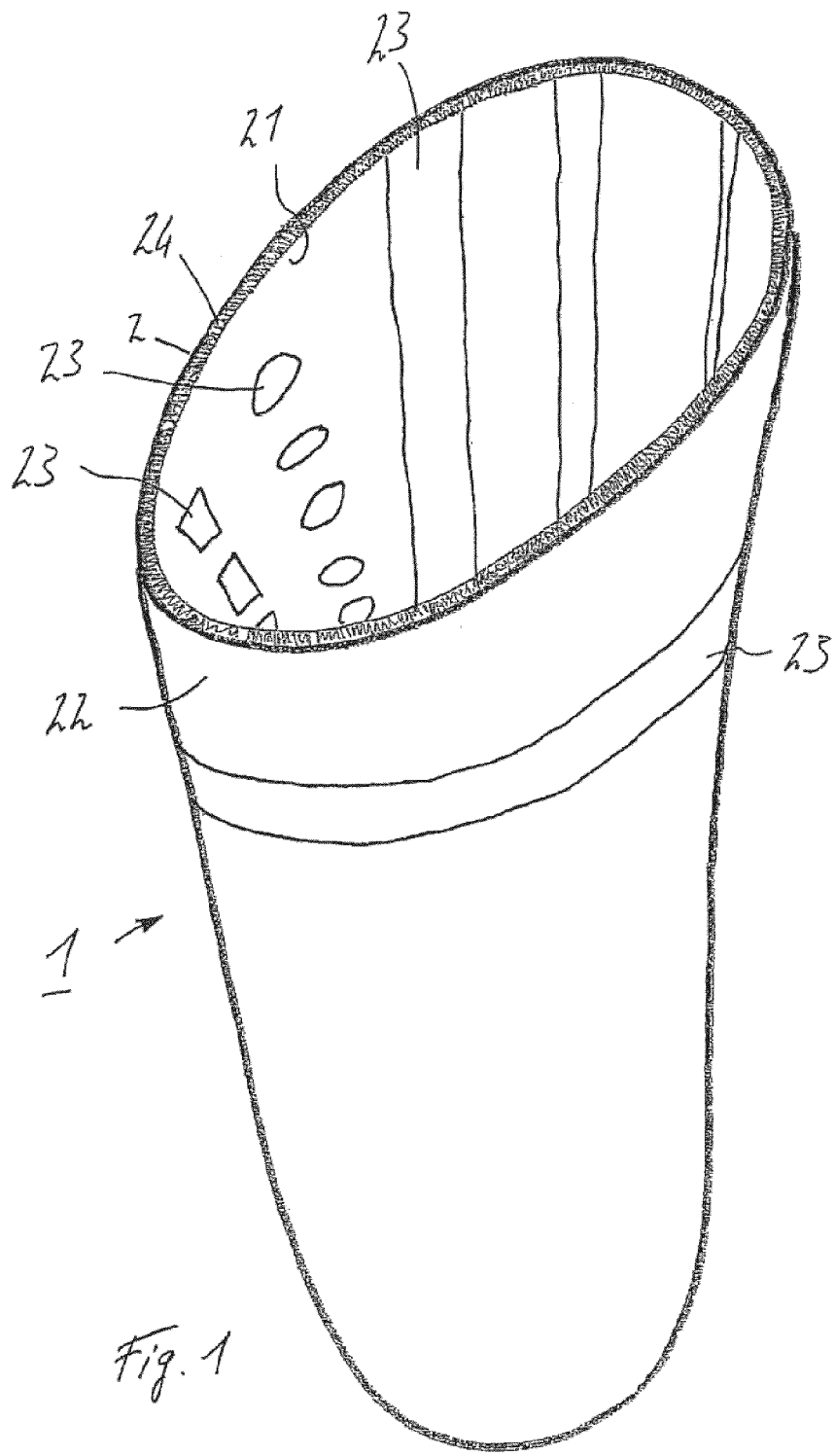
FIG. 1 shows a perspective view of an interface in the form of a liner.

FIG. 1 is a perspective and schematic view of an orthopedic interface 1 in the form of a liner, which is anatomically preshaped to fee applied to an amputation stump. The orthopedic interface 1 is made from a 3D textile, in the present case in the form of a spaced knitted fabric 2, composed of a bottom 21, which faces the skin of the interface user and is made of a lower textile, and with an upper textile on the top 22 facing away from the skin, between which supporting threads 24 are arranged that hold the upper and lower textiles 22, 21 at a distance from each other and connect them. If no upper textiles are present in the 3D textile, the respective top and bottom are labeled by reference signs 22, 21, such that the upper and lower textiles 22, 21 thus correspond to the top and bottom. Between the upper and lower textiles 22, 21, the supporting threads 24 form a well-ventilated space. Other 3D textiles, for example spaced knitted fabrics without lower and upper textiles or with only one lower or upper textile, can also be used. The interface 1 can be produced from a blank by sewing. It is likewise possible to connect the blank in another way, for example by adhesive bonding or welding.

On the inner surface of the interface 1, areas with an adhesive coating 23 are applied that adhere to the skin of the interface user, for example to an amputation stump. These coatings 23 can be in the shape of lines, dots, circles or squares. It is also possible in principle for the whole of the inner surface of the liner, i.e. the surface of the lower textile 21, to be provided with a coating 23. When the coating is applied only in some areas, improved transport of moisture from the skin of the user to the environment is obtained, thereby ensuring enhanced comfort, whereas a complete coating 23 of the surface provides improved adherence on account of the increased adhesion surface.

Coatings 23 that can be used are in particular silicone coatings, polyurethane coatings, or coatings made of a copolymer, although it is in principle also possible to provide other coatings that bring about improved adhesion of the lower textile 21, and thus of the 3D textile 1, to the surface of the skin.

A coating 23 can also be provided on the upper textile 22, i.e. on the outer surface of the liner or of the orthopedic interface. This coating can likewise be made of an adhesive material, the outer surface of the liner or of the interface 1 thus being provided with a coating that is chosen with respect to an orthopedic component arranged around it, for example a prosthesis socket or an orthotic holder. This also ensures improved adherence of the spaced knitted fabric 2 to the outer component. Elements with an interlocking action, for example nap velours or velcro areas, can also be arranged or formed on the upper textile 22.

Instead of a closed cross section, as shown in FIG. 1, the interface 1 can also have an open cross section, and a partially closed and partially open cross section can also be provided. It is also possible for closure devices to be arranged on the interface 1 so as to permit opening and closing and thus make the interface 1 easier to apply and remove.

FIG. 2 shows a holder 3 of a prosthesis, with a connecting branch 4 that connects the holder 3 to a joint device. The holder 3 has a tube-like, curved receiver part 30 with an open cross section and made of an elastic, stable plastic, with an outer surface 32 and an inner surface 31. On the inner surface 31 of the holder 3, there are coating areas 33 that are either made of an adhesive material or of a nap velour. It is likewise possible to provide several coatings 33 of different types. In principle, the whole of the inner surface 31 of the holder 3 can also be provided with a coating. The inner surface of the holder 3 can also be provided with alternative structures that offer less resistance in the direction of insertion of the interface than counter to the direction of insertion, for example suitably shaped form-fit elements that engage in correspondingly shaped structures in the interface.

FIG. 3 shows the holder 3 with the connecting branch 4 in engagement with the orthopedic interface 1. In the embodiment shown, the coating 33 of the holder 3 is designed as a nap velour and is oriented such that the orthopedic interface 1, configured as a liner for an amputation stump, can be inserted from above. The nap of the nap velour 33 is inclined downward, such that the orthopedic interface 1 can easily slide into the holder 3 but cannot slip out or cannot easily slip out. To release the orthopedic interface 1 from the holder 3, the latter is bent outward. The open cross section of the holder 3 can be bridged by straps or tensioning means in order to provide radial compression and stability. The partially open structure of the orthopedic interface 1 can likewise be bridged by closure devices.

FIG. 4 is an enlarged detail showing how the holder 3 interacts with the spaced knitted fabric 2 of the orthopedic interface 1. On the inner surface of the orthopedic interface 1, i.e. on the lower textile 21, there is an adhesive coating 23, for example of copolymer or silicone. The coating 23 applied is oriented in the longitudinal direction and permits a stable relationship of the surface of the skin to the interface 1. An air cushion and elastic padding are provided by the supporting threads 24. No coating is provided on the outer surface of the interface 1, i.e. on the upper textile 22, and coupling to the holder 3 is instead achieved by the nap velour 33, which is oriented in such a way that the orthopedic interface 1 can be inserted downward from the top, whereas pulling it out in the upward direction is made difficult or impossible.

The orthopedic interface 1 can also be used as a flexible socket or flexible socket part, and a suitable inner coating can also be provided for stockings or other support functions between a body part and an external device or an item of clothing or a functional unit, in order to ensure a uniform distribution of pressure over a large surface area of the body part with precise allocation and a high degree of comfort.

It has been surprisingly found that, despite the layer of air between the top and bottom, a good coupling of the orthopedic device, such as orthosis or prosthesis, and the interface user can be achieved, which was not previously considered possible. A 3D textile without an adhesive coating on the surface facing the skin can also be used as an orthopedic interface and provides a surprisingly high degree of comfort and security.

Figure 5:
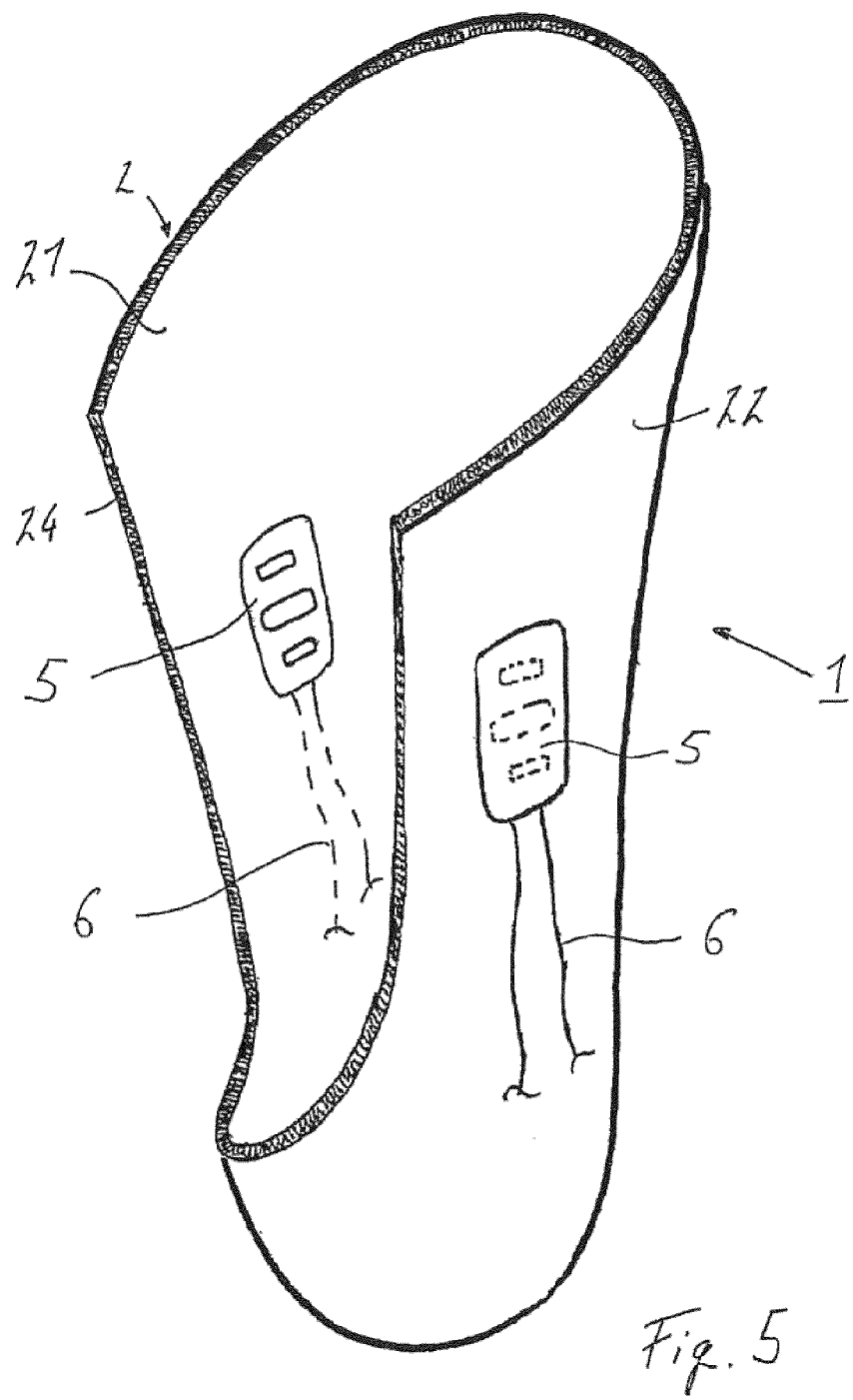
FIG. 5 shows a partially sectioned view of an alternative embodiment with electrodes.

FIG. 5 shows an alternative embodiment of the invention in which the orthopedic interface 1 is seen in a partial cross section. The structure of the 3D textile 2 corresponds to the one in FIGS. 1, 3 and 4, although the coatings that can be present on the inner or outer surfaces 21, 22 are not shown. Inside the orthopedic interface there are two electrodes 5 that are able to transmit data to an evaluation unit (not shown) via electrical connecting means 6. It is likewise possible to provide for wireless transmission of data from the electrodes 5. The electrodes 5 are arranged on the inner surface 21 of the spaced knitted fabric 2 and can be sewn, adhesively bonded, welded or otherwise secured thereon. Surface potentials are carried away via these electrodes 5, such that, for example, a prosthesis can be controlled via myoelectric signals. It is likewise possible for the electrodes 5 to be integrated inside the spaced knitted fabric 2, such that only the contact surfaces of the electrodes 5 with the skin surface protrude from the inner surface 21 of the 3D textile 2. The electrical connecting means 6 can be routed through recesses within the 3D textile 2 which is designed, for example, as a spaced knitted fabric. It is also possible to secure the electrodes by cutting a window out of the spaced knitted fabric 2 and placing the electrode into the window.

The invention claimed is:

1. An orthopedic interface for an orthotic or prosthetic device, comprising:
   a three dimensional (3D) textile with an outer surface and an inner surface wherein each of said outer surface and said inner surface are textiles and wherein a layer of air is positioned between said textiles of said outer surface and said inner surface;
   supporting threads, wherein said outer surface and said inner surface of said 3D textile are held at a distance from each other and connected to each other by said supporting threads; and
   a coating provided at least partially on said inner surface of said 3D textile configured to bear on skin of an interface user,
   wherein said orthopedic interface has a top and a bottom,
   wherein said outer surface of said 3D textile has a structure that is a nap velour which is oriented to have less resistance in a direction of insertion of the interface from the top to the bottom, than counter to the direction of insertion, and
   wherein at least one of
      areas of application of said coating on said inner surface of said 3D textile selected to improve exchange of heat and moisture from skin of an interface user through said interface to an environment outside of said outer surface of 3D textile, and
      a material used as said coating improves exchange of heat and moisture from skin of an interface user through said interface to an environment outside of said outer surface of 3D textile.

2. The orthopedic interface as claimed in claim 1, wherein said outer surface is configured to face away from the skin of said interface user, and wherein said outer surface is at least partially covered with said coating.

3. The orthopedic interface as claimed in claim 1, wherein the coating is composed of a material selected from the group consisting of silicone, polyurethane and a copolymer.

4. The orthopedic interface as claimed in claim 1, wherein the coating is electrically conductive.

5. The orthopedic interface as claimed in claim 1, wherein the coating is applied in multiple areas which are set apart from one another.

6. The orthopedic interface as claimed in claim 5 wherein at least some of said multiple areas are shaped in a shape selected from the group consisting of strips, dots, and rings.

7. The orthopedic interface as claimed in claim 1, wherein the coating is applied over said inner surface in said inner surface's entirety.

8. The orthopedic interface as claimed in claim 1, wherein the coating has a property selected from the group consisting of air-permeable and moisture-permeable.

9. The orthopedic interface as claimed in claim 1, wherein the threads of the 3D textile are at least partially coated.

10. The orthopedic interface as claimed in claim 1, wherein silver threads are woven or spun into the 3D textile.

11. The orthopedic interface as claimed in claim 10 wherein said silver threads are in said inner surface of said 3D textile.

12. The orthopedic interface as claimed in claim 1, wherein said 3D textile is configured as a liner for bearing on an amputation stump.

13. The orthopedic interface as claimed in claim 1, wherein said 3D textile is configured as a flexible socket or as a flexible socket part with receiving means for orthotic or prosthetic components.

14. The orthopedic interface as claimed in claim 1, wherein said 3D textile is anatomically preshaped.

15. The orthopedic interface as claimed in claim 1, wherein the 3D textile is a spaced knitted fabric.

16. The orthopedic interface as claimed in claim 1, further comprising electrodes applied to the inner surface or worked into the 3D textile.

17. The orthopedic interface as claimed in claim 1, wherein at least one of the 3D textile and the coating are antibacterial.

18. The orthopedic interface as claimed in claim 17 wherein said 3D textile or said coating includes a vapor deposition of silver or addition of silver ions.

19. A system, comprising:
   an orthopedic interface having
      a three dimensional (3D) textile with an outer surface and an inner surface wherein each of said outer surface and said inner surface are textiles and wherein a layer of air is positioned between said textiles of said outer surface and said inner surface;
      supporting threads, wherein said outer surface and said inner surface of said 3D textile are held at a distance from each other and connected to each other by said supporting threads; and
      a coating provided at least partially on said inner surface of said 3D textile configured to bear on skin of a user; and
   an orthotic or prosthetic device, wherein said orthotic or prosthetic device has a dimensionally stable receiver for receiving said orthopedic interface,
   wherein at least one of said outer surface of said 3D textile and an inside surface of said dimensionally stable receiver has a structure that is a nap velour which is oriented to have less resistance in a direction of insertion of the interface into the orthotic or prosthetic device than counter to the direction of insertion.

20. The system as claimed in claim 19, wherein said structure is on said inside surface of said receiver.

21. The system as claimed in claim 19, wherein said structure is on said outer surface of said 3D textile.

22. The system of claim 19 wherein at least one of
areas of application of said coating on said inner surface of said 3D textile selected to improve exchange of heat and moisture from skin of an interface user through said interface to an environment outside of said outer surface of 3D textile, and
a material used as said coating improves exchange of heat and moisture from skin of an interface user through said interface to an environment outside of said outer surface of 3D textile.

* * * * *